United States Patent [19]

Kruglikov et al.

[11] 3,956,184

[45] May 11, 1976

[54] METHOD OF PREPARING SILVER CATALYST FOR SYNTHESIS OF FORMALDEHYDE BY OXIDIZING METHYL ALCOHOL

[76] Inventors: Anatoly Abramovich Kruglikov, Vyazovskaya ulitsa, 9, kv. 9; Zemfira Ivanovna Yakovenko, ulitsa Lomonosova, 18, kv. 36; Marina Ivanovna Roznina, Gazetnaya ulitsa, 20, kv. 10; Anna Malofeevna Rogacheva, Pervomaiskaya ulitsa, 70a, kv. 32; German Ivanovich Belousov, Pervomaiskaya ulitsa, 70a, kv. 49, all of Nizhny Tagil Sverdlovskoi oblasti, U.S.S.R.

[22] Filed: Apr. 24, 1974

[21] Appl. No.: 463,794

[52] U.S. Cl. .................... 252/443; 252/455 R; 252/463; 252/476; 260/603 R
[51] Int. Cl.$^2$............................................ B01J 23/50
[58] Field of Search ........... 252/438, 463, 476, 443, 252/455 R; 260/603 R

[56] References Cited
UNITED STATES PATENTS

| | | | |
|---|---|---|---|
| 2,307,421 | 1/1943 | Overhoff | 252/476 |
| 2,424,083 | 7/1947 | Finch et al. | 252/476 X |
| 2,765,283 | 10/1956 | Sacken | 252/476 X |
| 2,805,229 | 9/1957 | Metzger | 252/476 X |
| 3,702,259 | 11/1972 | Nielsen | 252/463 X |

Primary Examiner—W. J. Shine
Attorney, Agent, or Firm—Holman & Stern

[57] ABSTRACT

The method of preparing a silver catalyst for synthesis of formaldehyde by oxidizing methyl alcohol which consists in that a carrier is impregnated with an aqueous or an aqueous-alcohol solution containing complex ions of silver having the general formula $[Ag(X)_n]^+$ or $[Ag(Y)_2]^-$, where X is ammonia, ethylenediamine, triethylenetetramine or triaminotriethylamine, Y is a thiocyanate, cyanide, acetate, or hydroxyl ion, and n is 1 or 2. The impregnated carrier is processed, at a temperature of from 10° – 100°C, with a reducing agent taken in the quantity sufficient to reduce the silver completely from said ion. The thus-prepared catalyst is dried at a temperature of from 80° to 400°C. It is recommended that the catalyst be washed with water before drying. The thus-prepared catalyst has a highly developed active surface with a small content of silver (the specific surface of the catalyst is 0.7 – 7 square meters per gram, with the metal silver content of the catalyst being from 5 – 10 per cent by weight). The catalyst is highly active and has good selectivity in the process of formaldehyde synthesis from methyl alcohol. The yield of formaldehyde with the proposed catalyst is from 75 – 80 per cent, calculating with reference to the passed methyl alcohol, with the selectivity of the process being from 89 – 95 per cent.

14 Claims, No Drawings

METHOD OF PREPARING SILVER CATALYST FOR SYNTHESIS OF FORMALDEHYDE BY OXIDIZING METHYL ALCOHOL

The invention relates to a method of preparing silver catalyst. Said catalyst is widely used in organic synthesis an in the preparation of formaldehyde from methyl alcohol, with the former being an important intermediate in the manufacture of synthetic resins, plastics, rubber, pentaerythritol and etc.

A method of preparing silver catalyst for synthesis of formaldehyde by oxidizing methyl alcohol is known in the prior art, which consists in the impregnation of a carrier with an aqueous solution of silver nitrate with the subsequent drying of the impregnated carrier and calcining same at a temperature of 650° – 700°C, during which the silver nitrate is decomposed into metallic silver and nitrogen oxides (cf. e.g., U.S. Pat. No. 1,067,665). The catalyst prepared by this method contains 35 – 50 percent by weight of metallic silver and has a specific surface of 0.2 – 6.4 sq.m/g.

The disadvantages inherent in this method of preparing silver catalyst are as follows:
1. High silver content of the catalyst, and hence high specific consumption of the precious metal for formaldehyde synthesis.
2. Significant energy consumption for drying the impregnated carrier and calcining it, with the greater share of heat being consumed at the calcining step.
3. Deterioration of the catalyst properties due to the high temperature at which the catalyst is calcined (650° – 700°C). At these temperatures, which are close to the melting point of silver, the active entities of the catalyst are fused and the metal drops penetrate into the pores of the catalyst carrier which partly clogs and smoothens the defects of the carrier crystal structure. All this decreases the active surface of the catalyst during the calcining step. Moreover, the catalyst surface area is also decreased due to the partial clogging of the carrier pores.
4. Low catalytic activity of the silver catalyst in the synthesis of formaldehyde from methyl alcohol. The yield of the end product obtained with said catalyst does not exceed 72 – 75 percent, calculating with reference to the passed methyl alcohol, with the selectivity of the process being 85 – 93 percent.
5. The catalyst begins to display its stable operation during the synthesis of formaldehyde from methyl alcohol in as long as 48 – 74 hours.

The object of this invention is to work out a method of preparing a silver catalyst for synthesis of formaldehyde by oxidizing methyl alcohol which would have large active surface and a low silver content.

Another object of the invention is to work out a method of preparing silver catalyst having high catalytic activity and selectivity in the process of formaldehyde synthesis from methyl alcohol.

Still another object of the invention is to work out a method which would make it possible to decrease significantly the power consumption in the preparation of the catalyst.

In accordance with these and other objects, the invention consists of impregnating of the carrier with an aqueous or an aqueous-alcohol solution (the water-to-alcohol ratio being from 10:90 to 90:10), containing complex ions of silver having the general formula $[Ag(X)_n]^+$ or $[Ag(Y)_2]^-$, where X is ammonia, ethylenediamine, triethylenetetramine or triaminotriethylamine, Y is a thiocyanate, cyanide, acetate or hydroxyl ion, and $n$ is 1 or 2; the impregnated carrier is then processed at a temperature of from 10° to 100°C with a reducing agent taken in a quantity sufficient for complete reduction of silver from said complex ions; the thus-prepared catalyst is then dried at a temperature of from 80° to 400°C.

The proposed method makes it possible to prepare highly active catalyst having a highly developed specific area (0.7 – 7 sq.m/g) with a silver content of the catalyst being from 5 to 10 percent by weight. The yield of formaldehyde with the proposed catalyst is 75 – 80 percent, calculating with reference to the methyl alcohol passed, with the selectivity of the process being from 89 – 95 percent.

As silver is reduced from the above-named complex ions, a fine metallic film is formed on the entire surface of the carrier. Such metallization of the developed surface of the carrier requires lower quantities of silver as compared with the known method.

Since the step of calcining is avoided altogether, then the power consumption of the process is decreased markedly, and moreover, no molten metal clogs the carrier pores, and all the defects inherent in the structure of the carrier remain unaffected. This ensures a high active surface for the catalyst.

From the standpoint of the theory of formaldehyde synthesis from methyl alcohol, which is known to proceed in the outer diffusion region, i.e., when the reaction rate largely depends on the magnitude of the catalyst surface and also on the accessibility of the surfaces to the reagents, it becomes a point of great importance that the catalyst should have a highly developed metallic surface. Making use of such a catalyst for the synthesis of formaldehyde ensures a high rate for the process and its high selectivity.

As it has already been said, an aqueous or an aqueous-alcohol solution containing complex ions of silver having the general formula $[Ag(X)_n]^+$ or $[Ag(Y)_2]^-$ are used to impregnate the carrier.

According to the invention, an aqueous or aqueous-alcohol solution containing complex ions of silver having the general formula $[Ag(X)_n]^+$, can be prepared by a process in which an aqueous or an aqueous-alcohol solution of a silver compound, such as its nitrate, sulphate, acetate, cyanide, or oxide, combined with is a complexing agent such as ammonia, ethylenediamine, triethylenetetramine, or triaminotriethylamine, in quantities sufficient for the formation of the said complex ions of silver and for the adjustment of the medium pH to the alkaline side.

Moreover, said aqueous or aqueous-alcoholic solution containing complex ions of silver having the general formula $[Ag(X)_n]^+$, can be prepared by a process in which to the aqueous or aqueous-alcohol solution of a silver compound, such as its nitrate, sulphate, acetate, cyanide, or oxide, is combined with an alkali to build up the alkaline medium, and then a complexing agent, such as ammonia, ethylenediamine, triethylenetetramine, or triaminotriethylamine is added in a quantity sufficient for the formation of said complex ions of silver.

The aqueous or aqueous-alcohol solution containing complex ions of silver having the general formula [Ag- $(Y)_2]^-$, where Y is a thiocyanate, cyanide, or acetate ion, can be prepared according to the invention as follows: an aqueous or aqueous-alcohol solution of silver nitrate, silver sulphate, silver acetate, silver cyanide, or silver oxide, is inoculated with thiocyanide, cyanide or an acetate of sodium or potassium in quantity required to prepare the above named silver complex ions of silver and to build up the alkaline medium.

The aqueous or aqueous-alcohol solution containing complex ions of silver having the general formula $[Ag(Y)_2]^-$, where Y is a thyocyanate, cyanide, or acetate ion can also be prepared as follows: an aqueous or aqueous-alcohol solution of silver nitrate, silver sulphate, silver acetate, silver cyanide or silver oxide, is inoculated with hydrocyanic, thiocyanic, or acetic acid in the quantity required to prepare said complex ions of silver and to ensure the acidic medium.

The aqueous or aqueous-alcohol solution containing complex ions of silver having the general formula $[Ag(Y)_2]^-$, where Y is a hydroxyl ion, can be prepared as follows: an aqueous or aqueous-alcohol solution of silver nitrate, silver sulphate, silver acetate, silver cyanide, or silver oxide, is inoculated with sodium hydroxide or potassium hydroxide in a quantity sufficient for the formation of said complex ions of silver and to ensure an alkaline reaction of the medium.

In the proposed method, it is recommendable to use hydrazine, hydrazine derivatives or formaldehyde in the gaseous state or in the form of their aqueous solution (preferably in the form of aqueous solutions) as reducing agents.

Moreover, it is also recommended that use be made of aqueous solutions of glucose, invert sugar or hydroxylamine be used as reducing agents.

It is recommended also that side reaction products and also non-reacted substances be removed from the catalyst surfaces by washing it with water after the reduction of the silver.

The drying temperature for the prepared catalyst should be (as it has already been specified) from 80° to 400°C. This drying temperature preserves the highly developed metallic surface of the catalyst and precludes sintering of the catalyst.

The proposed method of preparing silver catalyst for synthesis of formaldehyde by oxidizing methyl alcohol can be effected as follows:

First, a solution of silver nitrate, silver sulphate, silver acetate, silver cyanide, or argentous oxide is prepared. To that end the pre-calculated quantity of silver salt, or silver oxide, is dissolved in water or in an aqueous-alcohol solution (with the ratio of water to alcohol varying from 10:90 to 90:10; the alcohol can be either methyl, ethyl or n-propyl alcohol). The prepared solution of a silver salt or of silver oxide is used for preparing the impregnating aqueous or aqueous-alcohol solution containing the complex ions of silver having the general formula $[Ag(X)_n]^+$ or $[Ag(Y)_2]^-$, where X is ammonia, ethylenediamine, triethylenetetramine, or triaminotriethylamine, where Y is a thiocyanate, cyanide, acetate or hydroxyl ion, and $n$ is 1 or 2.

The aqueous or aqueous-alcohol solution containing the complex ions of silver having the general formula $[Ag(X)_n]^+$ can be prepared by a process in which the aqueous or aqueous-alcohol solution of silver salt or of silver oxide, is inoculated with a complexing agent, namely, ammonia, ethylenediamine, triethylenetetramine, or triaminotriethylamine taken in the quantity sufficient to prepare said complex ions of silver and to build up the required alkalinity in the solution.

Moreover, said aqueous-alcohol solution containing the complex ions of silver having the general formula $[Ag(X)_n]^+$ can be prepared by a process in which the aqueous or aqueous-alcohol solution of a silver salt, or of silver oxide is inoculated with alkali, for example, sodium hydroxide or potassium hydroxide, to build up the required alkalinity in the medium, and then the above complexing agent is added in the quantity required to prepare the above complex ions of silver.

Out of the above named complexing agents, ammonia is added into the solution of a silver salt or of silver oxide in the form of an aqueous solution or in the gaseous state, while ethylenediamine, triethylenetetramine and triaminotriethylamine are added per se.

The aqueous or aqueous-alcohol solutions containing complex ions of silver having the general formula $[Ag(Y)_2]^-$, where Y is a thiocyanate, cyanide, or acetate ion, can be prepared by a process in which the said aqueous or aqueous-alcohol solution of the silver salt or of silver oxide is inoculated with sodium thiocyanate, sodium cyanide, sodium acetate, or potassium thiocyanate, cyanide or acetate, in the quantities required to prepare said complex ions of silver and to build up the alkaline medium.

The aqueous or aqueous-alcohol solution containing the complex ions of silver having the general formula $[Ag(Y)_2]^-$, where Y is a thiocyanate, cyanide, or acetate ion, can be prepared also by a process in which the aqueous or aqueous-alcohol solution of the silver salt or of silver oxide, is inoculated with thiocyanic acid, hydrocyanic acid or acetic acid in the quantity required to prepare said complex ions of silver and to build up acid medium.

The aqueous or aqueous-alcohol solution containing complex ions of silver having the general formula $[Ag(Y)_2]^-$ where Y is a hydroxyl ion, can be prepared by a process in which the said aqueous or aqueous-alcohol solution of the silver salt or of silver oxide is inoculated with sodium hydroxide or potassium hydroxide, in which the alkalies are taken in the quantity required to prepare said complex ions of silver and to build up alkaline medium.

The prepared aqueous or aqueous-alcohol solutions containing the complex ions of silver is used to impregnate the carrier at a temperature of from 10° to 100°C. Natural alumosilicates, such as pumice, diatomaceous earth, perlite and also artificial alumosilicates (carborundum, corundum, silica gel) can be used as carriers. It is recommendable to use carriers with wide shallow pores having a specific area from 0.7 – 7 sq.m/g. The impregnated carrier is processed at a temperature of from 10° – 100°C with a reducing agent, during which the silver is reduced to pure metal and is deposited on the carrier surfaces. A wide range of reducing agents, such as hydrogen, potassium-sodium tartrate, sodium hypophosphite, p-methylaminophenol sulphate, Mohr's salt $FeSO_4·(NH_4)_2SO_4·6H_2O$, saccharose, or hypophosphorus acid, can be used according to the invention. The preferred reductants are: hydrazine, hydrazine derivatives (for example, hydrazine sulphate, hydrazine hydrate), formaldehyde (which are used in the gaseous state and in the form of their aqueous solutions), aqueous solutions of glucose, invert sugar, or hydroxylamine.

The thus-prepared catalyst is dried at a temperature of from 80° to 400°C and passed through a sieve, after which the catalyst is ready for use. As it has already been said, it is recommended to wash the catalyst of the products of side reactions and from unreacted substances before drying.

The carrier can be impregnated with aqueous or aqueous-alcohol solutions containing complex ions of silver (with subsequent reduction of silver and drying) several times to ensure uniform distribution of metallic silver on the developed surface of the carrier in the required quantities.

For a better understanding of the invention, the following examples of its practical embodiment are given by way of illustration.

EXAMPLE 1

An aqueous solution containing 1.312 g of silver nitrate in 125 ml of water was combined with 0.60 g of potassium hydroxide and 10 g of ethylenediamine. The silver ion $[Ag(H_2NCH_2CH_2NH_2)_2]^+$ complex was formed as a result. The thus prepared aqueous solution was used to impregnate, at a temperature of 10°C, 20 g of pumice in the form of granules sizing from 1.6 – 2.5 mm having a specific surface of 1.1 sq.m/g. The impregnated carrier was processed with 25 ml of a 10 percent solution of sodium-potassium tartrate. Silver was reduced to its pure state from the above complex ion at a pH of the solution of 9 – 10 and at a temperature of 22°C. The prepared catalyst was washed with water and dried at a temperature of 250°C for 20 minutes. The catalyst contained 3.2 percent by weight of metallic silver.

The procedure (application of silver metal to the carrier surface by impregnating it, reducing the silver, washing and drying) was repeated three times. The finished catalyst contained 9.6 percent by weight of silver metal and had a specific surface of 1.1 sq.m/g.

For the purpose of comparison, a silver catalyst was also prepared by the known method. To that end, 20 g of granulated (1.6 – 2.5 mm) pumice having a specific area of 1.1 sq.m/g were impregnated with 100 ml of an aqueous solution containing 20.12 g of silver nitrate. The impregnated carrier was dried, and then calcined at a temperature of 680°C for 2.5 hours until all the nitrogen oxides were removed. The prepared catalyst contained 38.7 percent by weight of silver metal and had a specific surface of 0.31 sq.m/g.

Both catalysts were tested in the synthesis of formaldehyde by oxidizing methyl alcohol with atmospheric oxygen. In both cases the concentration of the aqueous solution of methyl alcohol in the evaporator was 54 percent, the temperature of superheating the alcohol-air mixture was 120°C, the temperature in the contact zone was 650°C, the load on one square metre of the catalyst surface was 100 g of methyl alcohol per hour. The comparison of the results obtained with the two catalysts showed that the yield of formaldehyde with the catalyst prepared by the proposed method was 76.9 percent, calculating with reference to the passed methyl alcohol, with the selectivity of the process being 94 percent, while the yield of formaldehyde with the catalyst prepared by the known method was 74.9 percent, selectivity of 92.8 percent. The yield of formaldehyde with the catalyst prepared by the proposed method was thus 2 percent higher.

EXAMPLE 2

An aqueous solution containing 0.250 g of silver cyanide in 143 ml of water was inoculated with 0.0318 g of potassium cyanide. Complex silver ion $[Ag(CN)_2]^-$ was obtained as a result. The prepared aqueous solution containing said complex ion of silver was used to impregnate, at a temperature of 20°C, 20 g of granulated pumice (1.6 – 2.5 mm particle size) having a specific surface of 1.07 sq.m/g. The impregnated carrier was processed with 16.9 ml of a 10 percent solution of sodium hypophosphite (the reducing agent). Metallic silver was reduced on the surfaces of the carrier at pH 7 – 8 and at 90°C. The prepared catalyst was dried at a temperature of 300°C. The catalyst contained 0.9 percent by weight of silver metal.

The procedure of applying to the carrier surfaces was repeated seven times. The finished catalyst contained 6.3 percent by weight of metallic silver and had the specific surface of 1.07 sq.m/g.

For the purpose of comparison, a silver catalyst was also prepared according to the known method. To that end, 20 g of granulated (1.6 – 2.5 mm) pumice having the specific surface of 1.07 sq.m/g were impregnated with 100 ml of an aqueous solution containing 20.12 g of silver nitrate. The impregnated carrier was dried and then calcined at a temperature of 700°C for 2.5 hours until all the nitrogen oxides were removed. The prepared catalyst contained 38.7 percent by weight of silver metal and had a specific surface of 0.23 sq.m/g.

Both catalysts were tested in the synthesis of formaldehyde by oxidizing methyl alcohol under the conditions similar to those described in Example 1, except that the concentration of the aqueous solution of methyl alcohol in the evaporator was 69 percent and the temperature in the contact zone was 680°C. The comparison of the results showed that the yield of formaldehyde with the catalyst prepared according to the proposed method was 77.3 percent, calculating with reference to the methyl alcohol passed, at the selectivity of the process of 94.2 percent, while the yield of formaldehyde with the catalyst prepared by the known method was 72.3 percent, at the selectivity of 93.0 percent. The yield of formaldehyde with the catalyst prepared by the proposed method was thus 5 percent higher.

EXAMPLE 3

An aqueous solution of 10.48 g of silver nitrate in 40 ml of water was combined with 25 ml of a 25 percent aqueous solution of ammonia. Complex ion of silver $[Ag(NH_3)_2]^+$ was formed as a result. The prepared solution was used to impregnate, at a temperature of 25°C, 20 g of silica gel (granule size 1.6 – 2.5 mm) having a specific surface of 7.0 sq.m/g. The impregnated carrier was processed with 50 ml of a 37 percent solution of formaldehyde (reducing agent). The reduction of silver from the above named complex ion occurred at pH 10 – 11 and at a temperature of 22°C. The prepared catalyst was rinsed with water to neutral reaction, and dried at a temperature of 200°C. The finished catalyst contained 10 percent by weight of metallic silver and had a specific surface of 7.0 sq.m/g.

For the purpose of comparison a silver catalyst was also prepared by the known method; to that end 20 g of silicon gel of the same granule size and having the same specific area of 7.0 sq.m/g were impregnated with 100 ml of an aqueous solution containing 20.12 of silver nitrate. The impregnated carrier was dried and then calcined at a temperature of 700°C for 2.5 hours until all the nitrogen oxides were removed. The prepared catalyst contained 39 percent by weight of metallic silver and had the specific surface of 6.4 sq.m/g.

Both catalysts were tested in the synthesis of formaldehyde by the oxidizing methyl alcohol under the conditions similar to those described in Example 1, except that the concentration of the aqueous solution of methyl alcohol in the evaporator was 61 percent and the temperature in the contact zone was 700°C. The comparison of the results showed that the yield of formaldehyde with the catalyst prepared by the proposed method was 75.0 percent with respect to the methyl alcohol passed, with the selectivity of the process being 89.0 percent, while the yield of formaldehyde with the catalyst prepared by the known method was 73 percent with a selectivity of 86.0 percent. The yield of formaldehyde synthesized with the catalyst prepared by the proposed method was thus 2 percent higher.

EXAMPLE 4

An aqueous solution containing 5.56 g of silver nitrate in 120 ml of water was combined with 5 ml of a 10 percent aqueous solution of thiocyanic acid. The complex silver ion $[Ag(SCN)_2]^-$ was formed as a result. The prepared aqueous solution containing the above complex ion of silver was used to impregnate, at a temperature of 100°C, 20 g of diatomite in the form of granules sizing 1.0 – 3.0 mm, having a specific surface of 0.98 sq.m/g. The impregnated carrier was processed with 0.9 g of pyrogallic acid (reducing agent). The reduction of silver metal from the above complex ion occurred at pH 5 – 6 and at a temperature of 23°C. The prepared catalyst was washed with water to neutral reaction and dried at a temperature of 80°C. The finished catalyst contained 9.8 percent by weight of metallic silver and had the specific surface of 0.98 sq.m/g.

For the purpose of comparison a silver catalyst was also prepared by the known method. To that end 20 g of diatomite in the form of granules sizing 1.0 – 3.00 mm and having a specific surface of 0.98 sq.m/g were impregnated with 100 ml of an aqueous solution containing 20.12 g of silver nitrate. The impregnated carrier was dried and then calcined at a temperature of 700°C for 2.3 hours until all the nitrogen oxides were removed. The prepared catalyst contained 38.5 percent by weight of metallic silver and had a specific area of 0.29 sq.m/g.

Both catalyst were tested in the synthesis of formaldehyde by oxidizing methyl alcohol under the conditions similar to those described in Example 1, except that the concentration of the aqueous solution of methyl alcohol in the evaporator was 58 percent and the temperature in the contact zone was 680°C. The comparison of the results showed that the yield of formaldehyde with the proposed catalyst was 76.94 percent, calculated with reference to the methyl alcohol passed, while the yield of formaldehyde with the catalyst prepared by the known method was 73.94 percent, with the selectivity of the two processes being 89.7 and 85.6 percent, respectively. The yield of formaldehyde synthesized with the catalyst prepared by the proposed method was thus 3 percent higher.

EXAMPLE 5

128 ml of an aqueous-alcohol solution (n-propyl alcohol-to-water ratio 10:90) containing 0.64 g of silver nitrate was combined with 0.64 g of potassium hydroxide. The complex silver ion $[Ag(OH)_2]^-$ was prepared as a result. The prepared aqueous-alcohol solution containing the above silver ion was used to impregnate, at a temperature of 20°C, 20 g of pumice in the form of granules sizing from 1.6 to 2.5 mm and having a specific surface of 1.0 sq.m/g. The impregnated carrier was processed with 128 ml of an aqueous solution containing 0.32 g of inverted sugar (reducing agent). The reduction of silver from said complex ion of silver was effected at a medium pH of 11 – 12 and at a temperature of 25°C. The prepared catalyst was washed with water to a neutral reaction and dried at a temperature of from 180° to 190°C. The catalyst contained 2 percent by weight of metallic silver.

The procedure was repeated five times, after which the finished catalyst contained 10 percent by weight of metallic silver and had a specific surface of 1.0 sq.m/g.

For the purpose of comparison another silver catalyst was also prepared by the known method. To that end 20 g of granulated (1.6 – 2.5 mm) pumice having a specific surface of 1.0 sq.m/g wre impregnated with 100 ml of an aqueous solution containing 20.12 g of silver nitrate. The impregnated carrier was dried and then calcined at a temperature of 690°C for 2.5 hours until all the nitrogen oxides were removed. The prepared catalyst contained 38.4 percent by weight of metallic silver and had a specific surface of 0.4 sq.m/g.

Both catalysts were tested in the synthesis of formaldehyde by oxidizing methyl alcohol under conditions similar to those described in Example 1, except that the concentration of the aqueous solution of methyl alcohol in the evaporator was 52 percent, and the temperature in the contact zone was 700°C. The comparison of the results showed that the yield of formaldehyde with the catalyst prepared by the proposed method was 76.9 percent, calculated with reference to the methyl alcohol passed, with the selectivity of the process being 94.08 percent, while the yield of formaldehyde with the catalyst prepared by the known method was 73.0 percent, with a selectivity of 92.3 percent. The yield of formaldehyde with the catalyst prepared by the proposed method was thus 3.9 percent higher.

EXAMPLE 6

An aqueous solution containing 0.972 g of silver nitrate in 243 ml of water was combined with 0.608 g of sodium hydroxide and 5 g of triaminotriethylamine. The complex ion of silver

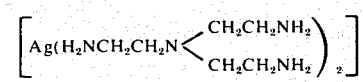

was thus prepared.

The prepared aqueous solution containing the above silver ion was used to impregnate, at a temperature of 30°C, 20 g of granulated (1.6 – 2.5 mm) pumice having a specific surface of 1.2 sq.m/g. The impregnated carrier was processed with 50 ml of a 37 percent solution of formaldehyde, in which 2.4 g of glucose had been dissolved. The reduction of silver from the above complex ion of silver occurred at pH = 10 – 11 and at a temperature of 24°C. The prepared catalyst was washed with water to a neutral reaction and dried at a temperature of 300°C. The catalyst contained 2.9 percent by weight of metallic silver.

The procedure was repeated three times. As a result the prepared catalyst contained 8.7 percent by weight of metallic silver and had a specific surface of 1.2 sq.m/g.

For the purpose of comparison another silver catalyst was also prepared by the known method. To that end 20 g of granulated pumice (1.6 – 2.5 mm) having the specific surface of 1.2 sq.m/g were impregnated with 100 ml of an aqueous solution containing 20.12 g of silver nitrate. The impregnated carrier was dried and then calcined at a temperature of 700°C for 2.5 hours until the nitrogen oxides were all removed. The finished catalyst contained 38.6 percent by weight of metallic silver and had a specific surface of 0.25 sq.m/g.

Both catalysts were tested in the synthesis of formaldehyde by oxidizing methyl alcohol under the conditions similar to those described in Example 1, except that the concentration of the aqueous solution of methyl alcohol in the evaporator was 63 percent, and the temperature in the contact zone was 700°C. The yield of formaldehyde with the catalyst prepared by the proposed method was 77.2 percent, calculating with reference to the methyl alcohol passed, with the selectivity of the process being 94.85, while the yield of formaldehyde with the catalysts prepared by the known method was 73.2 percent with a selectivity of 93.0 percent. The yield of formaldehyde synthesized with the catalyst prepared by the known method was thus 4 percent higher.

EXAMPLE 7

An aqueous solution containing 0.318 g of silver nitrate in 140 ml of water, was combined with 3.1 g of glacial acetic acid. The complex ion of silver $[Ag(CH_3COO)_2]^-$ was prepared as a result. The prepared solution containing said complex ion was used to impregnate, at a temperature of 20°C, 20 g of granulated (2 – 3 mm) pumice having a specific surface of 1.02 sq.m/g. The impregnated carrier was processed with 16 ml of a 10 percent aqueous solution of p-methylaminophenol-sulphate (reducing agent). The reduction of metallic silver from its complex ion was effected at a medium pH of 5 – 6 and at a temperature of 25°C. The prepared catalyst was washed with water to a neutral reaction and dried at a temperature of 90°C. The catalyst contained 0.95 percent by weight of metallic silver.

The procedure was repeated nine times, and the finished catalyst contained 8.55 percent by weight of metallic silver and had a specific surface of 1.02 sq.m/g.

For the purpose of comparison another silver catalyst was also prepared by the known method. To that end 20 g of granulated (2 – 3 mm) pumice having a specific surface of 1.02 sq.m/g were impregnated with 100 ml of an aqueous solution containing 20.12 g of silver nitrate. The impregnated carrier was dried and then calcined at a temperature of 700°C for 2.5 hours until the nitrogen oxides were all removed. The prepared catalyst contained 38.7 percent of metallic silver and had a specific surface of 0.24 sq.m/g.

Both catalyst were tested in the synthesis of formaldehyde by oxidizing methyl alcohol under the conditions similar to those described in Example 1, except that the concentration of the aqueous solution of methyl alcohol in the evaporator was 57 percent. The yield of formaldehyde obtained with these conditions with the catalyst prepared by the proposed method was 77.02 percent, calculating with reference to the methyl alcohol passed, with the selectivity of the process being 94.29 percent, while the yield of formaldehyde with the catalyst prepared by the known method was 75.0 percent with a selectivity of 92.8 percent. The yield of formaldehyde synthesized with the catalyst prepared by the proposed method was thus 2.02 percent higher.

EXAMPLE 8

100 ml of an aqueous-alcohol solution (ethyl alcohol-to-water ratio 90:10) containing 0.642 g of silver nitrate, was combined with 0.3 g of potassium hydroxide. The silver ion $[Ag(OH)_2]^-$ complex was prepared as a result. The prepared aqueous-alcohol solution containing said complex silver ion was used to impregnate, at a temperature of 30°C, 20 g of diatomite in the form of granules sizing from 1.6 – 2.5 mm, having and a specific surface of 2.6 sq.m/g. The impregnated carrier was processed with 105 ml of a 37 percent solution of formaldehyde in which 5 g of saccharose had been dissolved. The reduction of silver from its complex ion was effected at a solution pH of 9 – 10 and at a temperature of 24°C. The prepared catalyst was washed with water to neutral reaction and dried at a temperature of 200°C. The catalyst contained 2.5 percent by weight of metallic silver.

The procedure was repeated two times and the finished catalyst contained 5 percent by weight of metallic silver which had a specific surface of 2.6 sq.m/g.

For the purpose of comparison, another silver catalyst was also prepared by the known method. To that end 20 g of diatomite in the form of granules sizing from 1.6 – 2.5 mm, and having a specific surface of 2.6 sq.m/g, were processed with 100 ml of an aqueous solution containing 20.12 g of silver nitrate. The impregnated carrier was dried and then calcined at a temperature of 690°C for 2.5 hours until all the nitrogen oxides were removed. The prepared catalyst contained 38.1 percent by weight of metallic silver and had a specific surface of 1.5 sq.m/g.

Both catalysts were tested in the synthesis of formaldehyde by oxidizing methyl alcohol under the conditons similar to those described in Example 1, except that the temperature in the contact zone was 700°C. The yield of formaldehyde under these conditions with the catalyst prepared by the proposed method was 75.7 percent, calculating with reference to the methyl alcohol passed, with the selectivity of the process being 89.9 percent, while the yield of formaldehyde with the catalyst prepared by the known method was 74.7 percent with a selectivity of 86.0 percent. The yield of formaldehyde with the catalyst prepared by the proposed method was thus 1 percent higher.

EXAMPLE 9

An aqueous solution containing 5.42. g of silver acetate in 50 ml of water was combined with 0.54 g of potassium cyanide. The complex ion of silver $[Ag(CN)_2]^-$ was thus prepared. The solution was used to impregnate, at a temperature of 20°C, 20 g of granulated (2 – 3 mm) pumice having a specific surface of 1.05 sq.m/g. The impregnated carrier was processed with 42 ml of a 50 percent solution of hypophosphorous acid (reducing agent). The reduction of silver from its complex ion occurred at a solution pH of 7 – 8, and at a temperature of 90°C. The prepared catalyst was washed with water to a neutral reaction and dried at a temperature of 250°C. The finished catalyst contained 9.9 percent by weight of metallic silver and had a specific surface of 1.05 sq.m/g.

For the purpose of comparison, another silver catalyst was prepared by the method known in the prior art.

To that end, 20 g of granulated (2 – 3 mm) pumice having the specific surface of 1.05 sq.m/g, were processed with 100 ml of an aqueous solution containing 16.96 g of silver nitrate. The impregnated carrier was dried, and then calcined at a temperature of 700°C until all the nitrogen oxides were removed. The prepared catalyst contained 35 percent by weight of metallic silver and had a specific surface of 0.31 sq.m/g.

Both catalysts were tested in the synthesis of formaldehyde by oxidizing methyl alcohol under the conditions similar to those described in Example 1, except that the concentration of the aqueous solution of methyl alcohol in the evaporator was 59 percent and the temperature in the contact zone was 680°C. Under these conditions, the yield of formaldehyde with the catalyst prepared by the proposed method was 75.3 percent, calculating with reference to the methyl alcohol passed, with the selectivity being 94.3 percent, while the yield of formaldehyde with the catalyst prepared by the known method was 73.0 percent with a selectivity of 93.0 percent. The yield of formaldehyde with the catalyst prepared by the proposed method was thus 2.3 percent higher.

EXAMPLE 10

An aqueous solution containing 11.2 g of silver nitrate in 121 ml of water was combined with 10 g of triethylenetetramine. The silver ion complex $[Ag(H_2NCH_2CH_2NHCH_2CH_2NHCH_2CH_2NH_2)]^+$ was thus prepared. The solution containing the above silver ion complex was used to impregnate, at a temperature of 25°C, 20 g of granulated pumice (1.6 – 2.5 mm) having a specific surface of 0.7 sq.m/g. The impregnated carrier was processed with gaseous formaldehyde (reducing agent). The reduction of the metallic silver from its complex ion was effected at a solution pH of 8 and at a temperature of 24°C. The prepared catalyst was washed with water to a neutral reaction and dried at a temperature of 300°C. The finished catalyst contained 9.08 percent of by weight of metallic silver and had a specific surface of 0.7 sq.m/g.

For the purpose of comparison another silver catalyst was also prepared by the method known in the prior art. To that end, 20 g of granulated (1.6 – 2.5 mm) pumice having the specific surface of 0.7 sq.m/g were impregnated with 100 ml of an aqueous solution containing 20.12 g of silver nitrate. The impregnated carrier was dried and then calcined at a temperature of 680°C for 2.5 hours until all the nitrogen oxides were removed. The prepared catalyst contained 38.3 percent by weight of metallic silver and had a specific surface of 0.33 sq.m/g.

Both catalysts were tested in the synthesis of formaldehyde by oxidizing methyl alcohol under conditions similar to those described in Example 1, except that the concentration of the aqueous solution of methyl alcohol in the evaporator was 66 percent and the temperature in the contact zone was 670°C. Under these conditions, the yield of formaldehyde with the catalyst prepared by the method according to the invention was 77.01 percent, with the selectivity of the process being 94.29 percent, calculating with reference to the passed methyl alcohol, while the yield of formaldehyde with the catalyst prepared by the method known in the prior art was 73.01 percent, with the selectivity being 92.91 percent. The yield of formaldehyde with the catalyst prepared by the proposed method was thus 4 percent higher.

EXAMPLE 11

233 ml of an aqueous-alcohol solution (methyl alcohol-to-water ratio 20:80) containing 0.974 g of silver nitrate, was combined with 0.607 g of potassium hydroxide and 10 ml of a 25 percent solution of ammonia. The ion complex $[Ag(NH_3)_2]^+$ was thus prepared. The solution containing the above silver ion complex was used to impregnate, at a temperature of 20°C, 20 g of granulated (1.6 – 2.5 mm) pumice having a specific surface of 0.7 sq.m/g. The impregnated carrier was processed with 60 ml of an aqueous solution containing 0.6 g of glucose (reducing agent). The reduction of metallic silver from its complex ion was effected at a medium pH of 12–14 and at a temperature of 22°C. The prepared catalyst was washed with water to a neutral reaction and dried at a temperature of 200°C. The catalyst contained 2.85 percent by weight of metallic silver.

The procedure was repeated three times, and the finished catalyst contained 8.55 percent by weight of metallic silver and had a specific surface of 0.7 sq.m/g.

For the purpose of comparison another catalyst was also prepared by the method known in the prior art. To that end, 20 g of granulated pumice (1.6 – 2.5 mm) having the specific surface of 0.7 sq.m/g, were treated with 100 ml of an aqueous solution containing 20.12 g of silver nitrate. The impregnated carrier was dried and then calcined at a temperature of 700°C for 2.5 hours until all the nitrogen oxides were removed. The thus-prepared catalyst contained 39.95 percent of metallic silver and had a specific surface of 0.29 sq.m/g.

Both catalysts were tested in the synthesis of formaldehyde by oxidizing methyl alcohol under the conditions similar to those described in Example 1, except that the concentration of the aqueous solution of methyl alcohol in the evaporator was 75 percent and the temperature in the contact zone was 670°C. The comparison of the results showed that the yield of formaldehyde with the catalyst prepared by the proposed method was 77.05 percent, calculating with reference to the passed methyl alcohol, with the selectivity being 94.01 percent, while the yield of formaldehyde with the catalyst prepared by the known method was 73.1 percent with a selectivity of 92.03 percent. The yield of formaldehyde with the catalyst prepared according to the invention was thus 3.95 percent higher.

EXAMPLE 12

An aqueous solution containing 5.56 g of silver nitrate in 60 ml of water was combined with 16 ml of a 25 percent aqueous solution of ammonia. The complex ion of silver $[Ag(NH_3)_2]^+$ was thus formed. The prepared solution containing the above ion was used to impregnate, at a temperature of 20°C, 20 g of silica gel in the form of granules sizing 1.6 – 2.8 mm, and having a specific surface of 6.9 sq.m/g. The impregnated silica gel was processed with gaseous hydrazine (reducing agent). The reduction of metallic silver from its complex ion occurred at a medium pH of 10 – 12 and at a temperature of 100°C. The prepared catalyst was dried at a temperature of 200°C. The finished catalyst contained 9.89 percent by weight of metallic silver and had a specific surface of 6.9 sq.m/g.

For the purpose of comparison another silver catalyst was also prepared by the method known in the prior art. To that end, 20 g of granulated silica gel (1.6 – 2.8 mm) having a specific surface of 6.9 sq.m/g, were treated with 100 ml of an aqueous solution containing 20.12 g of silver nitrate. The impregnated carrier was dried and then calcined at a temperature of 700°C for 2.5 hours until all the nitrogen oxides were removed. The prepared catalyst contained 38.7 percent by weight of metallic silver and had the specific surface of 6.0 sq.m/g.

Both catalysts were tested in the synthesis of formaldehyde by oxidizing methyl alcohol under the conditions similar to those described in Example 1, except that the concentration of the aqueous solution of methyl alcohol in the evaporator was 55 percent and the temperature in the contact zone was 700°C. The comparison of the results showed that the yield of formaldehyde obtained with the catalyst prepared by the method according to the invention was 78.1 percent, calculating with reference to the methyl alcohol passed, with the selectivity being 89.2 percent, while the yield of formaldehyde with the catalyst prepared by the method known in the prior art was 72.2 percent, with a selectivity of 86.5 percent. The yield of formaldehyde with the catalyst prepared by the method according to the invention was thus 5.9 percent higher.

EXAMPLE 13

An aqueous solution containing 0.4 g of silver nitrate in 90 ml of water was combined with 0.25 g of sodium hydroxide and 10 ml of a 25 percent aqueous solution of ammonia. The complex ion of silver $[Ag(NH_3)_2]^+$ was thus formed. The prepared solution containing the above silver ion was used to treat, at a temperature of 30°C, 20 g of granulated pumice (1.6 – 2.5 mm) having a specific surface of 1.0 sq.m/g. The impregnated carrier was treated with 10 ml of an aqueous solution of hydroxylamine (concentration 2M/litre). The reduction of silver to metallic state from its complex ion occured at a medium pH of 13 – 14 and at a temperature of 21°C. The prepared catalyst was washed with water to a neutral reaction and dried at a temperature of 150°C. The catalyst contained 1 percent by weight of metallic silver.

The procedure was repeated ten times. The finished catalyst contained 10 percent by weight of metallic silver and had the specific surface of 1.0 sq.m/g.

For the purpose of comparison another silver catalyst was also prepared by the known method. To that end, 20 g of granulated (1.6 – 2.5 mm) pumice, having the specific surface of 1.0 sq.m/g. were treated with 100 ml of an aqueous solution containing 16.96 g of silver nitrate. The impregnated carrier was dried and then calcined at a temperature of 700°C for 2.5 hours until all the nitrogen oxides were removed. The prepared catalyst contained 35.1 percent by weight of metallic silver and had a specific surface of 0.3 sq.m/g.

Both catalysts were tested in the synthesis of formaldehyde by oxidizing methyl alcohol under the conditions similar to those described in Example 1, except that the concentration of the aqueous solution of methyl alcohol in the evaporator was 58 per cent and the temperature in the contact zone was 700°C. Under these conditions, the yield of formaldehyde with the catalyst prepared by the proposed method was 76.9 per cent calculating with reference to the methyl alcohol passed, with the selectivity of the process being 94.09 per cent, while the yield of formaldehyde with the catalyst prepared by the known method was 74 per cent, with a selectivity of 93.0 per cent. The yield of formaldehyde with the catalyst prepared by the method according to the invention was thus 2.9 per cent higher.

EXAMPLE 14

An aqueous solution containing 5.28 g of silver sulphate in 240 ml of water was combined with 6.48 g of glacial acetic acid. The complex ion of silver $[Ag(CH_3COO)_2]^-$ was thus prepared. The solution containing the above silver ion was used to treat, at a temperature of 15°C, 20 g of granulated (1.6 – 2.6 mm) pumice having a specific surface of 1.2 sq.m/g. The impregnated carrier was processed with a solution of 9.7 g of Mohr's salt in 50 ml of water. The reduction of metallic silver from the above complex ion occurred at a solution pH of 5 – 6 at and at a temperature of 10°C. The prepared catalyst was washed to a neutral reaction and dried at a temperature of 150°C. The finished catalyst contained 9.79 per cent by weight of metallic silver and had a specific surface of 1.2 sq.m/g.

For the purpose of comparison another silver catalyst was also prepared by the method known in the prior art. To that end 20 g of granulates (1.6 – 2.6 mm) pumice having the specific surface of 1.2 sq.m/g were treated with 100 ml of an aqueous solution containing 20.12 g of silver nitrate. The impregnated carrier was dried and then calcined at a temperature of 700°C for 2.5 hours until all the nitrogen oxides were removed. The prepared catalyst contained 38.91 per cent of metallic silver and had a specific surface of 0.2 sq.m/g.

Both catalysts were tested in the synthesis of formaldehyde by oxidizing methyl alcohol under the conditions similar to those described in Example 1, except that the concentration of the aqueous solution of methyl alcohol in the evaporator was 72 per cent. Under these conditions the yield of formaldehyde with the catalyst prepared by the method according to the invention was 75.1 per cent calculating with reference to the passed methyl alcohol, with the selectivity of the process being 94.8 per cent, while the yield of formaldehyde with the catalyst prepared by the known method was 73.1 per cent with a selectivity of 93.0 per cent. The yield of formaldehyde synthesized with the catalyst prepared by the method according to the invention was thus 2 per cent higher.

EXAMPLE 15

An aqueous solution containing 8.2 per cent of argentous oxide in 100 ml of water was combined with 0.82 g of sodium cyanide. The complex ion of silver $[Ag(CN)_2]^-$ was thus prepared. The solution containing the above silver ion was used to treat, at a temperature of 20°C, 20 g of granulated (1.6 – 2.8 mm) pumice having a specific surface of 1.19 sq.m/g. The impregnated carrier was treated with 37.2 g of sodium hypophosphite dissolved in 74 ml of water (reducing agent). The reduction of metallic silver from its complex ion occurred at pH of the solution of 7.5 and at a temperature of 94°C. The prepared catalyst was washed with water to a neutral reaction and dried at a temperature of 100°C. The prepared catalyst contained 9.9 per cent by weight of metallic silver and had a specific surface of 1.19 sq.m/g.

For the purpose of comparison another silver catalyst was also prepared by the method known in the prior art. To that end, 20 g of granulated (1.6 –2.8 mm) pumice having a specific surface of 1.19 sq.m/g, were treated with 100 ml of an aqueous solution containing 20.12 g of silver nitrate. The impregnated carrier was dried and then calcined at a temperature of 700°C until all the nitrogen oxides were removed. The prepared catalyst contained 38.41 per cent by weight of metallic silver and had a specific surface of 0.29 sq.m/g.

Both catalysts were tested in the synthesis of formaldehyde by oxidizing methyl alcohol under the conditions similar to those described in Example 1, except that the concentration of the aqueous solution of methyl alcohol in the evaporator was 60 per cent and the temperature in the contact zone was 660°C. The comparison of the results showed that the yield of formaldehyde with the catalyst prepared according to the invention was 76.0 per cent, calculating with reference to the methyl alcohol passes, with the selectivity of the process being 94.27 per cent, while the yield of formaldehyde with the catalyst prepared by the method known in a prior art was 74.0 per cent, with the selectivity of 92.85 percent The yield of formaldehyde with the catalyst prepared by the method according to the invention was thus 2 percent higher.

EXAMPLE 16

An aqueous solution containing 3.49 g of silver nitrate in 100 ml of water was combined with 0.3 g of sodium hydroxide. The complex ion of silver $[Ag(OH)_2]^-$ was thus prepared. The solution containing said complex ion of silver was used to impregnate, at a temperature of 22°C, 20 g of corundum in the form of granules sizing 1.6 – 2.5 mm, and having a specific surface of 1.11 sq.m/g. The impregnated carrier was processed with 30 ml of an aqueous solution containing 20 g of glucose (reducing agent). The reduction of metallic silver from its complex ion occurred at a pH of the solution of 12 –14, and at a temperature of 40°C. The prepared catalyst was washed with water to a neutral reaction and dried at a temperature of 400°C. The finished catalyst contained 9.8 per cent by weigth of metallic silver and had a specific surface of 1.11 sq.m/g.

For the purpose of comparison another silver catalyst was also prepared by the method known in the prior art. To that end, 20 g of corundum in the form of granules sizing 1.6 – 2.5 mm, and having the specific surface of 1.11 sq.m/g were treated with 100 ml of an aqueous solution containing 16.96 g of silver nitrate. The impregnated carrier was dried and then calcined at a temperature of 700°C for 2.5 hours until nitrogen oxides were all removed. The prepared catalyst contained 34.8 percent of metallic silver and had a specific surface of 0.2 sq.m/g.

Both catalysts were tested in the synthesis of formaldehyde by oxidizing methyl alcohol under the conditions similar to those described in Example 1, except that the concentration of the aqueous solution of methyl alcohol in the evaporator was 68 per cent and the temperature in the contact zone was 675°C. The comparison of the results showed that the yield of formaldehyde with the catalyst prepared by the method according to the invention was 76.8 per cent, calculating with reference to the methyl alcohol passed, with the selectivity of the process being 94.11 per cent, while the yield of formaldehyde with the catalyst prepared by the known method was 74.0 per cent with a selectivity of 92.49 per cent. The yield of formaldehyde synthesized with the catalyst prepared by the proposed method was thus 2.8 per cent higher.

EXAMPLE 17

An aqueous solution containing 5.56 g of silver nitrate in 60 ml of water, was combined with 20 ml of a 25 percent aqueous solution of ammonia. The complex ion of silver $[Ag(NH_3)_2]^+$ was thus prepared, and the solution containing said ion of silver was used to treat, at a temperature of 25°C, 20 g of carborundum, in the form of granules sizing 1.4 – 2.88 mm, and having a specific surface of 2.22 sq.m/g. The impregnated carrier was processed with gaseous hydrogen (reducing agent). The reduction of metallic silver from its complex ion occurred at solution pH of 12 –13 and at a temperature of 100°C. The prepared catalyst was dried at a temperature of 100°C. The catalyst contained 9.6 per cent by weight of metallic silver and had a specific surface of 2.22 sq.m/g.

For the purpose of comparison, another silver catalyst was also prepared by the method known in the prior art. To that end, 20 g of granulated (1.4 – 2.8 mm) carborundum having a specific surface of 2.22 sq.m/g were treated with 100 ml of an aqueous solution containing 20.12 g of silver nitrate. The impregnated carrier was dried and then calcined at a temperature of 700°C for 2.5 hours until all the nitrogen oxides were removed. The prepared catalyst contained 38.5 per cent of by weight of metallic silver and had a specific surface of 1.25 sq.m/g.

Both catalysts were tested in the synthesis of formaldehyde by oxidizing methyl alcohol under the conditions similar to those described in Example 1, except that the concentration of the aqueous solution of methyl alcohol in the evaporator was 71 percent. Under these conditions, the yield of formaldehyde with the catalyst prepared by the proposed method was 75.0 percent calculating with reference to the methyl alcohol passed, with the selectivity of the process being 93.08 percent, while the yield of formaldehyde with the catalyst prepared by the method known in the prior art was 73.0 percent with a selectivity of 88.01 percent. The yield of formaldehyde with the catalyst prepared by the method according to the invention was thus 2 percent higher.

EXAMPLE 18

An aqueous solution containing 5.56 g of silver nitrate in 40 ml of water was inoculated with 20 ml of a 25 percent aqueous solution of ammonia. The complex ion of silver $[Ag(NH_3)_2]^+$ was prepared as a result, and the solution containing this complex ion was used to treat, at a temperature of 30°C, 20 g of granulated (1.6 – 2 mm) pumice having a specific surface of 1.01 sq.m/g. The impregnated carrier was processed with 100 ml of an aqueous solution containing 16 g of hydrazine hydrate (reducing agent). The reduction of metallic silver from its complex io occurred at a solution pH of 14 and at a temperature of 20°C. The prepared catalyst was washed with water to a neutral reaction and dried at a temperature of 80°C. The finished catalyst contained 9.7 per cent by weight of metallic silver and had a specifice surface of 1.01 sq.m/g.

For the purpose of comparison another silver catalyst was prepared by the method known in the prior art. To that end, 20 g of granulated (1.6 – 2 mm) pumice having the specific surface of 1.01 sq.m/g were treated with 100 ml of an aqueous solution containing 20.12 g of silver nitrate. The impregnated carrier was dried, and then calcined at a temperature of 700°C for 2.5 hours until all the nitrogen oxides were removed. The prepared catalyst contained 38.2 percent by weight of metallic silver and had a specific surface of 0.2 sq.m/g.

Both catalysts were tested in the synthesis of formaldehyde by oxidizing methyl alcohol under the conditions similar to those described in Example 1, except that the concentration of methyl alcohol in the evaporator was 60 percent and the temperature in the contact zone was 670°C. The comparison of the results showed that the yield of formaldehyde with the catalyst prepared by the proposed method was 80.0 per cent calculating with reference to the methyl alcohol passed, with the selectivity of the process being 94.9 percent, while the yield of formaldehyde in the process with the catalyst prepared by the known method was 73.1 per cent with a selectivity of 92.8 percent. The yield of formaldehyde with the catalyst prepared by the method according to the invention was thus 6.9 percent higher.

EXAMPLE 19

An aqueous solution containing 249.12 g of silver nitrate in 4 litres of water was inoculated with 800 ml of a 25 percent aqueous solution of ammonia. The complex ion of silver $[Ag(NH_3)_2]^-$ was prepared as a result, and the solution containing this ion was used to impregnate, at a temperature of 20°C. 3 kg of granulated (2.5 – 5 mm) pumic having a specific surface of 1.2 sq.m/g. The impregnated carrier was treated with 2 litres of an aqueous solution containing 112 g of hydraulic sulphate (reducing agent). The reduction of metallic silver from its complex ion occurred at a solution pH of 13 – 14 and at a temperature of 40 – 50°C. The prepared catalyst was washed with water to a neutral reaction until no sulphate ion was detected in the washings, after which it was dried at a temperature of 400°C. The catalyst contained 4.9 per cent by weight of metallic silver.

The procedure was repeated two times. The finished catalyst contained 9.8 percent of metallic silver and had a specific surface of 1.2 sq.m/g.

For the purpose of comparison another catalyst was also prepared by the method known in the prior art. To that end, 3 kg of pumice (granules sizing 2.5 – 5 mm), having a specific surface of 1.2 sq.m/g, were treated with 5.4 litres of an aqueous solution containing 3 kg of silver nitrate. The impregnated carrier was dried and then calcined at a temperature of 680°C for 2.5 hours until all the nitrogen oxides were removed. The prepared catalyst contained 37.8 percent of metallic silver and had a specific surface of 0.37 sq.m/g.

Both catalysts were tested in the synthesis of formaldehyde by oxidizing methyl alcohol under the conditions similar to those described in Example 1, except that the concentration of the methyl alcohol solution in the evaporator was 64.5 percent, and the temperature in the contact zone was 690°C. The comparison of the results showed that the yield of formaldehyde with the catalyst prepared in accordance with the present invention was 79.5 percent, with reference to the methyl alcohol passed, with the selectivity of the process being 95.0 percent, while the yield of formaldehyde with the catalyst prepared by the known method was 73.0 percent with a selectivity of 92.7 percent. The yield of formaldehyde with the catalyst prepared by the proposed method was thus 6.5 percent higher.

EXAMPLE 20

An aqueous solution containing 2.1 g of silver sulphate in 90 ml of water was inoculated with 10 ml of a 25 percent solution of ammonia in water. The complex ion of silver $[Ag(NH_3)_2]^+$ was thus prepared, and the solution containing this complex ion was used to treat granulated (1.6 – 3.0 mm) pumice having a specific surface of 0.9 sq.m/g. The impregnated carrier was treated with 60 ml of an aqueous solution containing 2.4 g of hydrazine sulphate (reducing agent). The reduction of metallic silver from its ion occurred at a solution pH of 13 and at a temperature of 60°C. The prepared catalyst was washed with water to a neutral reaction and dried at a temperature of 210°C. The finished catalyst contained 9.6 percent by weight of metallic silver and had specific surface of 0.9 sq.m/g.

For the purpose of comparison another silver catalyst was also prepared by the method known in the prior art. To that end, 15 g of granulated (1.6 – 3.0 mm) pumice having the specific surface of 0.9 sq.m/g were treated with 60 ml of an aqueous solution containing 15.9 g of silver nitrate. The impregnated carrier was dried and then calcined at a temperature of 690°C for 2.5 hours until all the nitrogen oxides were removed. The prepared catalyst contained 37.9 percent by weight of metallic silver and had a specific surface of 0.34 sq.m/g.

Both catalysts were tested in the synthesis of formaldehyde by oxidizing methyl alcohol under the conditions similar to those described in Example 1, except that the concentration of the aqueous solution of methyl alcohol in the evaporator was 62 per cent and the temperature in the contact zone was 680°C. In these conditions the yield of formaldehyde with the catalyst prepared by the proposed method was 78 percent, calculating with reference to the passed methyl alcohol, with the selectivity of the process being 95.0 percent, while the yield of formaldehyde with the catalyst prepared by the known method was 73.5 per cent with a selectivity of 92.9 percent. The yield of formaldehyde with the catalyst prepared by the proposed method was thus 4.5 percent higher.

What is claimed is:

1. A method of preparing a silver catalyst for the synthesis of formaldehyde which comprises:
   a. mixing a solution selected from the group consisting of an aqueous solution and an aqueous-alcohol solution having a volume ratio of water to alcohol of from 10:90 to 90:10 of a silver compound selected from the group consisting of silver nitrate, silver sulphate, silver acetate, silver cyanide and argentous oxide with a complexing agent selected from the group consisting of ammonia, ethylenediamine, triethylenetetramine and triaminotriethylamine, said complexing agent being added to the solution in a quantity sufficient to produce an alkaline pH and for the formation of complex ions of silver having the general formula $[Ag(X)_n]^+$ where X is ammonia, ethylenediamine, triethylenetetramine or triaminotriethylamine and $n$ is 1 or 2;
   b. impregnating a carrier with the resulting solution from step (a) at a temperature of from 10° to 100°C;
   c. treating the impregnated carrier at a temperature of from 10° to 100°C with a reducing agent taken in a quantity sufficient for the complete reduction of metallic silver from said complex ions; and d. drying the thus-prepared catalyst at a temperature of from 80° to 400°C.

2. A method of preparing a silver catalyst for the synthesis of formaldehyde which comprises:
a. combining a solution selected from the group consisting of an aqueous solution and an aqueous-alcohol solution having a volume ratio of water to alcohol of from 10:90 to 90:10 of a silver compound selected from the group consisting of silver nitrate, silver sulphate, silver acetate, silver cyanide and argentous oxide with an alkali metal compound selected from the group consisting of sodium hydroxide and potassium hydroxide to produce an alkaline pH, and then with a complexing agent selected from the group consisting of ammonia, ethylenediamine, treithylenetetramine and triaminotriethylamine, said complexing agent being added to the solution in an amount sufficient for the formation of complex ions of silver having the general formula $[Ag(X)_n]^+$ where X is ammonia, ethylenediamine, triethylenetetramine or triaminotriethylamine and $n$ is 1 or 2;
b. impregnating a carrier with the resulting solution from step (a) at a temperature of from 10° to 100°C;
c. treating the impregnated carrier at a temperature of from 10° to 100°C with a reducing agent taken in a quantity sufficient for the complete reduction of metallic silver from said complex ions; and
d. drying the thus-prepared catalyst at a temperature of from 80° to 400°C.

3. A method of preparing a silver catalyst for the synthesis of formaldehyde which comprises:
a. mixing a solution selected from the group consisting of an aqueous solution and an aqueous-alcohol solution having a volume ratio of water to alcohol of from 10:90 to 90:10 of a silver compound selected from the group consisting of silver nitrate, silver sulphate, silver acetate, silver cyanide and argentous oxide with a salt of an alkali metal selected from the group consisting of thiocyanates, cyanides and acetates of sodium and potassium, said salt of an alkali metal being added in an amount sufficient to produce an alkaline pH and the formation of complex ions of silver having the general formula $[Ag(Y)_2]^-$ where Y is a thiocyanate, cyanide or acetate ion;
b. impregnating a carrier with the resulting solution from step (a) at a temperature of from 10° to 100°C;
c. treating the impregnated carrier at a temperature of from 10° to 100°C with a reducing agent taken in a quantity sufficient for the complete reduction of metallic silver from said complex ions; and
d. drying the thus-prepared catalyst at a temperature of from 80° to 400°C.

4. A method of preparing a silver catalyst for the synthesis of formaldehyde which comprises:
a. mixing a solution selected from the group consisting of an aqueous solution and an aqueous-alcohol solution having a volume ratio of water to alcohol of from 10:90 to 90:10 of a silver compound selected from the group consisting of silver nitrate, silver sulphate, silver acetate, silver cyanide and argentous oxide with an acid selected from the group consisting of thiocyanic, hydrocyanic and acetic acid, said acid being added in an amount sufficient to produce an acid pH and for the formation of complex ions of silver having the general formula $[Ag(Y)_2]^-$ where Y is thiocyanate, cyanide or acetate ion;
b. impregnating a carrier with the resulting solution from step (a) at a temperature of from 10° to 100°C;
c. treating the impregnated carrier at a temperature of from 10° to 100°C with a reducing agent taken in a quantity sufficient for the complete reduction of metallic silver from said complex ions; and
d. drying the thus-prepared catalyst at a temperature of from 80° to 400°C.

5. A method of preparing a silver catalyst for the synthesis of formaldehyde which comprises:
a. mixing a solution selected from the group consisting of an aqueous solution and an aqueous-alcohol solution having a volume ratio of water to alcohol of from 10:90 to 90:10 of a silver compound selected from the group consisting of silver nitrate, silver sulphate, silver acetate, silver cyanide and argentous oxide with an alkali metal compound selected from the group consisting of sodium hydroxide and potassium hydroxide, said alkali being added in an amount sufficient to produce an alkaline pH and for the formation of complex ions of silver having the general formula $[Ag(Y)_2]^-$ where Y is hydroxyl ion;
b. impregnating a carrier with the resulting solution from step (a) at a temperature of from 10° to 100°C;
c. treating the impregnated carrier at a temperature of from 10° to 100°C with a reducing agent taken in a quantity sufficient for the complete reduction of metallic silver from said complex ions; and
d. drying the thus-prepared catalyst at a temperature of from 80° to 400°C.

6. The method of claim 2 wherein a compound selected from the group consisting of hydrazine, hydrazine sulphate, hydrazine hydrate and formaldehyde, in the gaseous state and in the form of their aqueous solutions, is used as the reducing agent.

7. The method of claim 3 wherein a compound selected from the group consisting of hydrazine, hydrazine sulphate, hydrazine hydrate and formaldehyde, in the gaseous state and in the form of their aqueous solutions, is used as the reducing agent.

8. The method of claim 4 wherein a compound selected from the group consisting of hydrazine, hydrazine sulphate, hydrazine hydrate and formaldehyde, in the gaseous state and in the form of their aqueous solutions, is used as the reducing agent.

9. The method of claim 5 wherein a compound selected from the group consisting of hydrazine, hydrazine sulphate, hydrazine hydrate and formaldehyde, in the gaseous state and in the form of their aqueous solutions, is used as the reducing agent.

10. A method according to claim 1, in which compounds selected from the group consisting of hydrazine, hydrazine sulphate, hydrazine hydrate, and formaldehyde, in the gaseous state and in the form of their aqueous solutions, are used as reducing agents.

11. A method according to claim 1, in which aqueous solution of compounds selected from the group consisting of glucose, inverted sugar, and hydroxylamine, are used as reducing agents.

12. A method according to claim 1, in which before drying, the catalyst is washed with water.

13. A method according to claim 1, in which natural aluminosilicates, selected from the group consisting of pumice, and diatomite are used as carriers.

14. A method according to claim 1, in which artificial aluminosilicates, selected from the group consisting of carborundum, corundum, and silica gel, are used as carriers.

\* \* \* \* \*